United States Patent [19]

Jakobson et al.

[11] Patent Number: 5,397,497

[45] Date of Patent: Mar. 14, 1995

[54] BATH ADDITIVE COMPOSITION CONTAINING POLYGLYCEROL FATTY ACID ESTER MIXTURE

[75] Inventors: Gerald Jakobson; Werner Siemanowski, both of Rheinberg; Karl-Heinz Uhlig, Krefeld-Traar, all of Germany

[73] Assignee: Solvay Fluor und Derivate GmbH, Hannover, Germany

[21] Appl. No.: 101,066

[22] Filed: Aug. 4, 1993

[30] Foreign Application Priority Data

Aug. 7, 1992 [DE] Germany .................. 42 26 173.2

[51] Int. Cl.$^6$ .................. C11D 7/50; C11D 3/50
[52] U.S. Cl. .................. 252/170; 252/174.11; 252/173; 252/DIG. 5
[58] Field of Search ............. 252/89.1, 174.11, 174.24, 252/173, DIG. 5, 170, 171

[56] References Cited

U.S. PATENT DOCUMENTS

| | | | |
|---|---|---|---|
| 4,529,605 | 7/1985 | Lynch et al. | 514/552 |
| 5,130,056 | 7/1992 | Jakobson et al. | 252/551 |
| 5,247,114 | 9/1993 | Jakobson et al. | 554/227 |

*Primary Examiner*—Paul Lieberman
*Assistant Examiner*—Lorna M. Douyon
*Attorney, Agent, or Firm*—Evenson, McKeown, Edwards & Lenahan

[57] ABSTRACT

A bath additive composition, in particular an oil bath preparation, containing at least one surface-active component, preferably a water-soluble emulsifier, at least one oily or oil-containing component selected from the natural and synthetic, mineral, ethereal and fatty animal and vegetable oils, optionally a solvent or solvent mixture and also further auxiliaries and additives, the bath additive preparation containing 10 to 60 wt-% of a polyglycerol fatty acid ester mixture as the water-soluble emulsifier and/or solubilizer, 10 to 60 wt-% of an oil, oil mixture and/or oil component having cosmetic and/or therapeutic activity and 0 to 70 wt-% of water, the polyglycerol fatty acid ester mixture containing 0 to 5 parts by weight diglycerol fatty acid esters, 20 to 65 parts by weight triglycerol fatty acid esters, 20 to 50 parts by weight tetraglycerol fatty acid esters, and 5 to 40 parts by weight higher polyglycerol fatty acid esters, for a total of 100 parts by weight, and the fatty acid component consisting of one or more fatty acids selected from the saturated and/or unsaturated, branched and/or unbranched $C_6$- to $C_{14}$- fatty acids containing less than 10 wt-% fatty acids having more than 14 carbon atoms.

11 Claims, No Drawings

BATH ADDITIVE COMPOSITION CONTAINING POLYGLYCEROL FATTY ACID ESTER MIXTURE

BACKGROUND OF THE INVENTION

The present invention relates to a bath additive composition, in particular an oil bath preparation, containing at least one surface-active component, preferably a water-soluble emulsifier, at least one oily or oil-containing component selected from the natural and synthetic, mineral, ethereal and fatty animal and vegetable oils, optionally a solvent or solvent mixture, and optionally further additives and/or adjuvants.

Baths containing added bath preparations having a suitable cosmetic, therapeutic and/or physiological effect (bath additive preparations) are enjoying increasing popularity, since they not only serve to clean the body, but also have a regenerating and normalizing effect on the skin due to their content of skin care ingredients, and have a refreshing, relaxing and possibly healing effect on the human body due to their content of medicinal or therapeutic additives, such as, for example, ethereal oils. Bath preparations of this type are also called oil or skin-care baths. Moreover, they can also contain perfuming additives.

Bath preparations of this type are supplied in solid, liquid (including gelatinous and highly viscous) or pasty form. Liquid preparations are preferably used which frequently take the form of aqueous or oily emulsions or dispersions. They customarily contain the following primary constituents: at least one surface-active compound which acts as a surfactant, emulsifying, dispersing, solubilizing and/or wetting agent and is either largely water-soluble or largely fat-soluble; at least one active compound which exerts a caring, protecting, regenerating, vitalizing and/or medicinal therapeutic effect, and optionally an aqueous or organic solvent or solvent mixture.

Pure cosmetic active ingredients include, for example, additives based on lipids and other creaming, oil-restoring substances which affect the water-binding power of the skin. These also include certain vegetable and animal oils which have cosmetic properties. A medicinal therapeutic effect on the human body can be achieved, for example, by means of specific ethereal oils or vegetable extracts.

As further constituents, bath additive preparations can contain foam improvers and enhancers, pH regulators, preservatives having antiseptic, bactericidal or bacteriostatic properties, antioxidants, thickeners or viscosity regulators, colorants and/or fragrances.

The bath preparations are added to the bath water in accordance with appropriate dosage instructions, the preparation being adjusted to assure a uniform distribution of the constituents of the formulation in the bath water or spreading of the preparation on the surface of the water.

Bath preparations in accordance with the prior art are disadvantageous in two different respects.

On the one hand, it is difficult to incorporate oily and oil-containing additives, especially natural or identical-to-natural ethereal or fatty vegetable oils, in cosmetic and pharmaceutical preparations since it is difficult to emulsify substances of this type. Therefore, it is necessary to use special emulsifiers or emulsifier mixtures. In the prior art, these were primarily ethylene oxide addition compounds which, although they have good emulsifying properties, are less desirable because of their toxicological and dermatological properties, and in particular cannot exert cosmetic effects.

On the other hand, known bath preparations which are intended to have both a cosmetic and a medicinal or therapeutic utility, usually have a complicated and expensive recipe.

In addition, emulsifiers which are suitable not only for preparing stable oil/water systems, such as, for example, bath oil formulations, but which also exert a physiological action, in particular a skin-caring and/or skin-protecting effect, have not been available in sufficient amounts.

SUMMARY OF THE INVENTION

It is the object of the present invention to provide an improved bath additive preparation.

Another object of the invention is to provide a bath additive composition which is particularly suitable as an oil bath preparation.

A further object of the invention is to provide a cosmetic bath additive composition which exerts skin-care, skin-protecting and/or a skin-regenerating action on the human skin.

It is also an object of the invention to provide a bath additive composition which exerts a therapeutic effect on the human body.

An additional object of the invention is to provide a bath additive composition which has a simple recipe in which a water-soluble, liquid emulsifier is used.

Yet another object of the invention is to provide a bath additive composition which is non-toxic and dermatologically acceptable.

These and other objects of the invention are achieved in accordance with the present invention by providing a bath additive composition comprising 10 to 60 wt-% of at least one water-soluble surface-active component, 10 to 60 wt-% of at least one oily or oil-containing component having cosmetic or therapeutic activity selected from the group consisting of natural and synthetic, mineral, ethereal and fatty animal and vegetable oils, and 0 to 70 wt-% water, wherein the at least one surface-active component is a polyglycerol fatty acid ester mixture consisting of 0 to 5 parts by weight diglycerol fatty acid esters, 20 to 65 parts by weight triglycerol fatty acid esters, 20 to 50 parts by weight tetraglycerol fatty acid esters, and 5 to 40 parts by weight higher polyglycerol fatty acid esters, for a total of 100 parts by weight, in which the fatty acid consists of at least one fatty acid selected from the group consisting of saturated and unsaturated, branched and unbranched $C_6$- to $C_{14}$- fatty acids containing less than 10 wt-% of fatty acids having more than 14 carbon atoms.

DETAILED DESCRIPTION OF PREFERRED EMBODIMENTS

The bath preparation according to the invention contains at least one polyglycerol fatty acid ester as a surface-active constituent. Compounds of this type or mixtures of polyglycerol fatty acid esters are known as solubilizers and emulsifiers or dispersing agents in cosmetic and pharmaceutical preparations and in foodstuffs. Until now, however, no polyglycerol fatty acid ester mixture has been available which exists as a liquid, water-soluble product and has an HLB of over 8, so that is suitable for the preparation of stable oil/water systems, in particular for emulsifying ethereal and fatty vegetable or animal oils in bath preparations, and which has a narrow distribution with respect to the glycerol oligomers employed.

Surprisingly, it has now been found that a bath additive preparation according to the present invention, in particular an oil bath preparation, fulfills all of the objects set forth above. The bath additive composition in accordance with the present invention is characterized in that it comprises:

10 to 60 wt-% of→a polyglycerol fatty acid ester mixture as a water-soluble emulsifier and/or solubilizer;
10 to 60 wt-% of→an oil, oil mixture and/or oil component which has a cosmetic and/or therapeutic effect; and
0 to 70 wt-% of→water,
said polyglycerol fatty acid ester mixture consisting of:
0 to 5 parts by weight diglycerol fatty acid esters,
20 to 65 parts by weight triglycerol fatty acid esters,
20 to 50 parts by weight tetraglycerol fatty acid esters, and
5 to 40 parts by weight higher polyglycerol fatty acid esters, for a total of 100 parts by weight, and said fatty acid ester mixture containing as the fatty acid component thereof at least one fatty acid selected from the group consisting of $C_6$- to $C_{14}$- fatty acids containing less than 10 wt-% fatty acid having more than 14 carbon atoms. The fatty acid component may be saturated and/or unsaturated and branched and/or unbranched.

In particular, the polyglycerol fatty acid ester mixture employed used in accordance with the invention takes on a double function. On the one hand it has an HLB of above 8 and is outstandingly suitable for emulsifying and solubilizing oily and oil-containing substances, particularly ethereal and fatty vegetable oils, so that it is possible to establish phase equilibria which completely satisfy all usual criteria with respect to stability.

The outstanding emulsifying action of the polyglycerol fatty acid ester mixture according to the invention is also retained when the bath additive preparation according to the invention is incorporated in highly dilute aqueous solutions, such as, for example, bath water, whereby it surprisingly has been found that spontaneous emulsification of the oily or oil-containing component takes place.

On the other hand, the polyglycerol fatty acid ester mixture according to the invention is not only physiologically acceptable and readily biodegradable, but it also has a skin-caring and skin-protecting action, particularly an oil-restoring effect, which gives the skin a pleasant feeling after the bath even when the bath additive preparation according to the invention has been highly diluted in the bath water, and counteracts the tendency of the bath water to dry out the skin.

Because of this double function of the polyglycerol fatty acid ester mixture according to the invention, the bath additive preparation of the invention has a cosmetic action with respect to protection and care of the skin as a result of the presence of just the polyglycerol fatty acid ester mixture alone, and the addition of a further oil, oil mixture and/or oil component which has a cosmetic effect and/or therapeutic effect gives, depending on the oil, oil mixture or oil component employed, an increased cosmetic effect and/or has a healing, relieving, tranquilizing and/or vitalizing physiological effect.

Even if the composition consists of only two constituents, namely the emulsifier employed in accordance with the invention and an oil or oil mixture having a therapeutic effect, it is possible to provide an oil bath formulation using the bath additive preparation according to the invention which has a cosmetic and a medicinal therapeutic effect and additionally causes spontaneous emulsification of the oil in the bath water.

In a bath prepared using the bath additive preparation according to the invention, the constituents of the oil bath formulation are finely dispersed in the bath water and/or on the water surface (spreading) and can therefore optimally achieve their intended effect. The phase equilibria established by the polyglycerol fatty acid ester mixture according to the invention are not disturbed either by the usual strongly varying temperature conditions in the bath water or by electrolytes, in particular inorganic salts, dissolved in the water.

The bath additive preparation according to the invention also constitutes an ecologically advantageous oil bath formulation since residues of the bath additive preparation contained in the used bath water are readily biodegradable, and the emulsifier employed according to the invention is also completely physiologically acceptable.

In accordance with a preferred embodiment, the bath additive preparation of the invention contains 15 to 50 wt-% of a polyglycerol fatty acid ester mixture,
15 to 50 wt-% of an oil, oil mixture and/or oil component which has a cosmetic and/or therapeutic effect, and
0.5 to 60 wt-% of water;
wherein the polyglycerol fatty acid ester mixture contains:
0 to 3 parts by weight diglycerol fatty acid esters,
22 to 32 parts by weight triglycerol fatty acid esters,
39 to 49 parts by weight tetraglycerol fatty acid esters, and
24 to 34 parts by weight higher polyglycerol fatty acid esters; and
the fatty acid component consists of one or more fatty acids selected from the group consisting of saturated and unsaturated, branched and unbranched $C_8$- to $C_{12}$- fatty acids containing less than 5 wt-% of fatty acids having more than 14 carbon atoms.

Bath additive preparations according to the invention preferably contain caprylic acid, capric acid, lauric acid, undecenoic acid, 2-ethylhexanoic acid or coconut fatty acid as the fatty acid component in the polyglycerol fatty acid ester mixture according to the invention. It is also possible in accordance with the invention for the foregoing fatty acids to be present as mixtures with one another. Additional or particular properties can be provided in the polyglycerol fatty acid ester mixture according to the invention by means of the aforementioned fatty acid compounds. These include, for example, either particular skin-care properties or, as in the case of undecenoic acid, an antimycotic action, which is advantageous for preservation of the bath additive preparation.

In accordance with a further preferred embodiment, the bath additive composition according to the invention contain at least one fatty vegetable oil, preferably jojoba oil, soya oil, sesame oil, groundnut oil, sunflower oil, olive oil, palm oil, palm kernel oil, castor oil, cocoa oil, coconut oil, almond oil or wheatgerm oil, as the oil having a cosmetic effect, these oils being employed either individually or in mixtures with one another.

In addition, the bath additive preparation according to the invention may contain animal oils as the oil having cosmetic activity. For example, one preferred animal oil is synthetic uropygial gland oil, which has the effect of rendering the skin hydrophobic.

Using these natural or identical-to-natural oils or oil mixtures, the bath additive compositions according to the invention are provided with skin-caring, skin-protecting and/or skin-regenerating effects which supplement the cosmetic properties, particularly the oil-restoring properties, of the polyglycerol fatty acid ester mixture according to the invention.

Particular pharmacological or medicinal therapeutic properties are provided in the bath additive preparation according to the invention by the use of oils or oil mixtures which have an appropriate activity, preferably by addition of ethereal oils, such as rosemary oil, lavender oil, balm mint oil, sage oil, garlic oil, juniper berry oil, aniseed oil, cardamon oil, pimento oil, aniseed oil, caraway oil, lemon oil, orange oil, peppermint oil, camphor oil, pine-needle oil or eucalyptus oil, these oils being employed either individually or in mixtures with one another. These oils impart a medicinal activity to the bath additive composition according to the invention in that they exert a relieving or healing action on the human body and/or exhibit their therapeutic activity by means of a relaxing, refreshing or vitalizing effect.

According to a further preferred embodiment, the bath additive preparation according to the invention contains natural or synthetic compounds, such as isopropyl myristate, isopropyl palmirate, decyl oleate, cetyl stearyl isononanoate, 2-octyldodecanol, lanolin or cholesterol derivatives or caprylic/capric acid triglyceride as the oil and/or oil component having a cosmetic effect, these compounds being employed either individually or in mixtures with one another and also having a skin-caring and/or oil-restoring action.

The aforementioned natural or synthetic, fatty vegetable and animal oils and also ethereal oils and oil components can be used as complete or partial replacements for each other in the bath additive preparation according to the invention. They may also be completely or partially replaced in the bath additive preparation according to the invention by mineral oils or oil mixtures which have a pharmaceutical or therapeutic effect, such as, for example, liquid paraffin.

An additional perfuming effect can be provided in the bath additive preparation according to the invention by the addition of certain ethereal oils, preferably rose oil, jasmine oil, violet oil, mimosa oil, orange oil, neroli oil, patchouli oil, sandalwood oil or cinnamon oil and also by addition of synthetic or natural perfume compositions, these oils or perfume compositions being employed either individually or in mixtures with one another. In this way a so-called scented bath is obtained.

Solutions of vegetable extracts, such as those of camomile, can be contained in the bath additive preparation as further therapeutically active substances in order, for example, to relieve or to heal inflammation of the skin and/or in the respiratory tract organs.

The bath additive preparation according to the invention can also be formulated as a foam bath. To achieve this, foaming agents are additionally incorporated, such as, for example, anionic surfactants, preferably alkyl ether sulfonates and sulfates, in particular sodium lauryl ether sulfate, in order to obtain a good foaming power even in the presence of substantial amounts of fats or oils.

As the solvent, the bath additive preparation according to the invention can preferably contain demineralized water which optionally contains small amounts of water-soluble organic solvents which are acceptable in health terms. Such organic solvents include, for example, glycerol and/or lower alcohols, such as 1,2-propanediol, which can be employed as additional solubilizers and prevent turbidity due to flocculation of organic constituents in the bath additive preparation.

It is particularly advantageous to use small amounts of water as a solvent if the bath additive preparation of emulsifying or solubilizing polyglycerol fatty acid ester mixture according to the invention and the oily or oil-containing component forms a turbid solution. An optically clear solution is then obtained by the addition of water.

The polyglycerol fatty acid ester mixture according to the invention exhibits its superiority compared with conventional, commercially available products particularly with respect to its excellent solubilizing power in water-containing oil bath preparations.

The polyglycerol fatty acid ester mixture according to the invention may additionally be combined with a further polyglycerol fatty acid ester mixture as a solubilizer. To do this, a polyglycerol caprate or a polyglycerol cocoate, preferably prepared according to our co-pending U.S. patent application Ser. No. 07/838,330, now U.S. Pat. No. 5,247,114 the entire disclosure of which is incorporated herein by reference, is particularly suitable.

When the vegetable oil content is high, particularly in a water-containing preparation, it may be advantageous to protect the bath additive preparation according to the invention against microbial decay. Compounds such as benzoates, benzoic acid derivatives, sorbates, microbiologically active phenols, such as 2,6-di-tert-butyl-4-methylphenol, and dioxanes, such as 5-bromo-5-nitro-1,3dioxane, can be employed as bacteriostatic or bactericidal preservatives.

To protect the bath additive preparation according to the invention against oxidative decomposition, antioxidants, such as tocopherols, in particular vitamin E, and/or butyl-hydroxytoluene, can be included in the composition. These preservatives are employed in the bath additive preparation according to the invention in customary amounts.

Further additives or adjuvants contained in the bath additive compositions according to the invention may include pH regulators, thickeners or viscosity regulating agents, such as polyglycols, propylene glycol, ethanol, isopropanol, and/or inorganic salts, preferably sodium chloride, complexing agents for masking metal ions and coloring agents.

The pH of the bath additive preparation is preferably between 5.5 and 7.5, depending on the water content.

The bath additive preparation according to the invention displays its advantageous action in particular in an amount of from 15 to 30 ml in about 200 liters of bath water.

The bath additive composition according to the invention is prepared by simply mixing the constituents in appropriate mixing devices; the sequence of addition of the individual components is not critical.

The polyglycerol fatty acid ester mixture according to the invention is obtained by a modification of the process disclosed in our co-pending U.S. patent application Ser. No. 08/089820, filed Jul. 12, 1993, (Attorney Docket No. 173/41298; claiming priority of Federal Republic of Germany application no. P 42 23 407.7), the disclosure of which is incorporated herein by reference.

The process is modified by esterifying a polyglycerol containing per 100 parts by weight:

0 to 5 parts by weight diglycerol,
20 to 65 parts by weight triglycerol,
20 to 50 parts by weight tetraglycerol, and
5 to 40 parts by weight higher polyglycerols, with one or more fatty acids selected from the saturated and/or unsaturated, branched and/or unbranched $C_6$- to $C_{14}$-fatty acids, the fatty acid or the fatty acid mixture having a content of less than 10 wt-% of fatty acids having more than 14 carbon atoms, in a molar ratio of the polyglycerol to the fatty acid or to the fatty acid mixture of 4:1 to 1:1 in accordance with said U.S. patent application Ser. No. 08/089820 and optionally working up the resulting polyglycerol fatty acid ester mixture.

Preferably, a polyglycerol which contains per 100 parts by weight:

0 to 3 parts by weight diglycerol,
22 to 32 parts by weight triglycerol,
39 to 49 parts by weight tetraglycerol, and
24 to 34 parts by weight higher polyglycerols is esterified with one or more fatty acids selected from the saturated and/or unsaturated, branched and/or unbranched $C_8$- to $C_{12}$- fatty acids, the fatty acid or the fatty acid mixture containing less than 5 wt-% of fatty acids having more than 14 carbon atoms, in a molar ratio of the polyglycerol to fatty acid or fatty acid mixture of from 2.5:1 to 1.5:1, preferably 2:1, in accordance with said U.S. patent application Ser. No. 08/089820, and optionally working up the resulting polyglycerol fatty acid ester mixture.

The following examples are intended to illustrate the invention in further detail without restricting its scope.

Example 1

Oil-restoring Pine-needle Oil Bath Composition

A composition was prepared comprising:
45 wt-% polyglycerol caprylcaprate according to the invention;
20 wt-% pine-needle oil, and
35 wt-% water (fully demineralized).

Example 2

Spreading Oil Bath Composition with High Skincare Action

A composition was prepared comprising:
20 wt-% polyglycerol caprate according to the invention;
20 wt-% polyglycerol caprate (prepared according to U.S. Pat. No. 5,247,114)
20 wt-% isopropyl myristate;
31 wt-% viscous liquid paraffin GP;
5 wt-% perfume oil, and
4 wt-% water (fully demineralized).

Example 3

Spontaneously Emulsifying Skin-care Oil Bath Composition

A composition was prepared comprising:
25 wt-% polyglycerol caprate according to the invention;
17 wt-% polyglycerol cocoate (prepared according to U.S. Pat. No. 5,247,114)
33 wt-% isopropyl myristate;
20 wt-% jojoba oil, and
5 wt-% perfume oil.

Example 4

Spontaneously Emulsifying Scented Bath Composition

A composition was prepared comprising:
45 wt-% polyglycerol caprate according to the invention;
10 wt-% isopropyl myristate;
10 wt-% perfume oil (Frey & Lau "Creme Bouquet"), and
35 wt-% water (fully demineralized).

Example 5

Water-soluble Oil Foam Bath Composition

A composition was prepared comprising:
20 wt-% polyglycerol caprate according to the invention;
10 wt-% isopropyl myristate;
50 wt-% sodium lauryl ether sulfate (28 % active content);
10 wt-% rosemary oil;
5 wt-% 1,2-propanediol, and
5 wt-% water (fully demineralized).

Example 6

Water-soluble Oil Foam Bath Composition

A composition was prepared comprising:
20 wt-% polyglycerol caprylcaprate according to the invention;
10 wt-% isopropyl myristate;
50 wt-% sodium lauryl ether sulfate (28 % active content);
10 wt-% lavender oil;
5 wt-% 1,2-propanediol, and
5 wt-% water (fully demineralized).

Example 7

Spontaneously Emulsifying Skin-care Oil Bath Composition

A composition was prepared comprising:
55 wt-% polyglycerol caprate according to the invention;
2 wt-% polyglycerol cocoate (prepared according to U.S. Pat. No. 5,247,114)
13 wt-% isopropyl myristate;
12 wt-% juniper berry oil, and
18 wt-% water (fully demineralized).

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A bath additive composition comprising:
   10 to 60 wt-% of at least one water-soluble surface-active component,
   10 to 60 wt-% of at least one oily or oil-containing component which has cosmetic or therapeutic activity selected from the group consisting of natural and synthetic, mineral, ethereal and fatty animal and vegetable oils, and
   0 to 70 wt-% water, wherein said at least one surface lactive component is a liquid polyglycerol fatty acid ester mixture consisting of:
- 0 to 5 parts by weight diglycerol fatty acid esters,
- 20 to 65 parts by weight triglycerol fatty acid esters,
- 20 to 50 parts by weight tetraglycerol fatty acid esters, and
- 5 to 40 parts by weight higher polyglycerol fatty acid esters, for a total of 100 parts by weight, in which the fatty acid consists of at least one fatty acid selected from the group consisting of saturated and unsaturated, branched and unbranched $C_6$- to $C_{14}$- fatty acids containing less than 10 wt-% of fatty acids having more than carbon atoms.

2. A composition according to claim 1, further comprising at least one solvent.

3. A composition according to claim 1, wherein said surface-active component is a water-soluble emulsifier.

4. A composition according to claim 1, wherein said composition is an oil bath preparation.

5. A composition according to claim 1, comprising:
- 15% to 50 wt-% of polyglycerol fatty acid ester mixture,
- 15 to 50 wt-% of at least one oil, oil mixture or oil component which exerts a cosmetic or therapeutic effect, and
- 0.5 to 60 wt-% of water, wherein said polyglycerol fatty acid ester mixture consists of:
- 0 to 3 parts by weight diglycerol fatty acid esters,
- 22 to 32 parts by weight triglycerol fatty acid esters,
- 39 to 49 parts by weight tetraglycerol fatty acid esters, and
- 24 to 34 parts by weight higher polyglycerol fatty acid esters, for a total of 100 parts by weight, in which the fatty acid consists of at least one fatty acid selected from the group consisting of saturated and unsaturated, branched and unbranched $C_8$- to $C_{12}$-fatty acids containing less than 5 wt-% fatty acids having more than 14 carbon atoms.

6. A composition according to claim 1, wherein said fatty acid consists of at least one fatty acid selected from the group consisting of caprylic acid, capric acid, lauric acid, undecenoic acid, 2-ethylhexanoic acid and coconut fatty acid.

7. A composition according to claim 1, wherein said oily or oil-containing component comprises at least one oil selected from the group consisting of jojoba oil, soya oil, sesame oil, groundnut oil, sunflower oil, olive oil, castor oil, palm oil, palm kernel oil, cocoa oil, coconut oil, almond oil and wheatgerm oil.

8. A composition according to claim 1, wherein said oily or oil-containing component comprises at least one ethereal oil selected from the group consisting of rosemary oil, lavender oil, balm mint oil, sage oil, garlic oil, juniper berry oil, aniseed oil, cardamon oil, pimento oil, caraway oil, lemon oil, orange oil, peppermint oil, camphor oil, clove oil, pine-needle oil and eucalyptus oil.

9. A composition according to claim 1, wherein said oily or oil-containing component comprises at least one compound selected from the group consisting of isopropyl myristate, isopropyl palmitate, decyl oleate, cetyl stearyl isononanoate, 2-octyldodecanol, lanolin derivatives, cholesterol derivatives and caprylic-capric acid triglyceride.

10. A composition according to claim 1, further comprising a perfuming component.

11. A composition according to claim 10, wherein said perfuming component is selected from the group consisting of rose oil, jasmine oil, violet oil, mimosa oil, orange oil, neroli oil, patchouli oil, sandalwood oil and cinnamon oil.

* * * * *